US009498156B2

(12) United States Patent
Whitehurst et al.

(10) Patent No.: US 9,498,156 B2
(45) Date of Patent: Nov. 22, 2016

(54) OPACITY CONSISTENT POLYMER GRAFT FOR OPTICAL SENSOR

(71) Applicant: Senseonics, Incorporated, Germantown, MD (US)

(72) Inventors: Todd Whitehurst, Germantown, MD (US); Philip Huffstetler, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 41 days.

(21) Appl. No.: 14/279,759

(22) Filed: May 16, 2014

(65) Prior Publication Data

US 2014/0343381 A1 Nov. 20, 2014

Related U.S. Application Data

(60) Provisional application No. 61/824,637, filed on May 17, 2013.

(51) Int. Cl.

*A61B 5/1455* (2006.01)
*A61B 5/145* (2006.01)
*A61B 5/1459* (2006.01)
*A61B 5/00* (2006.01)

(52) U.S. Cl.

CPC ........... *A61B 5/1455* (2013.01); *A61B 5/1459* (2013.01); *A61B 5/14532* (2013.01); *A61B 5/14552* (2013.01); *A61B 5/0031* (2013.01); *A61B 2562/162* (2013.01)

(58) Field of Classification Search

CPC ............ A61B 5/1455; A61B 5/14532; A61B 5/6846

See application file for complete search history.

(56) References Cited

U.S. PATENT DOCUMENTS

| | | | | |
|---|---|---|---|---|
| 6,330,464 | B1 | 12/2001 | Colvin, Jr. et al. | |
| 6,702,857 | B2 * | 3/2004 | Brauker | A61B 5/14532 424/424 |
| 7,713,745 | B2 | 5/2010 | Colvin, Jr. et al. | |
| 7,943,219 | B2 | 5/2011 | Krueger | |
| 2008/0220436 | A1 | 9/2008 | Holmes-Davis et al. | |
| 2011/0236989 | A1 * | 9/2011 | Suri | G01N 21/6428 436/172 |
| 2011/0303121 | A1 | 12/2011 | Geim et al. | |
| 2013/0331667 | A1 * | 12/2013 | Colvin, Jr. | A61B 5/14532 600/316 |

* cited by examiner

*Primary Examiner* — Eric Winakur

(74) *Attorney, Agent, or Firm* — Rothwell, Figg, Ernst & Manbeck, P.C.

(57) ABSTRACT

A sensor (e.g., an optical sensor) that may be placed within a living animal (e.g., a human) and may be used to measure an analyte (e.g., glucose or oxygen) in a medium (e.g., interstitial fluid) within the animal. The sensor may include a sensor housing and a polymer graft including indicator molecules and covering at least a portion of the sensor housing. The opacity of the polymer graft may remain substantially the same (i.e., may have little or no variation) over time. The sensor may include a photodetector, and variation in the opacity of the polymer graft does not cause a significant change in a measurement signal output by the photodetector. The polymer hydrogel may be made of polymers including acrylic acid and/or polyethylene glycol.

31 Claims, 8 Drawing Sheets

OPACITY CONSISTENT POLYMER GRAFT FOR OPTICAL SENSOR

CROSS-REFERENCE TO RELATED APPLICATIONS

The present application claims the benefit of priority to U.S. Provisional Application Ser. No. 61/824,637, filed on May 17, 2013, which is incorporated herein by reference in its entirety.

BACKGROUND

Field of Invention

The present invention relates generally to sensors for implantation within a living animal and measurement of a concentration of an analyte in a medium within the living animal. Specifically, the present invention relates to sensors having a polymer graft including indicator molecules on the surface of the sensor body, where the opacity of the graft does not vary over time.

Discussion of the Background

A sensor may be implanted within a living animal (e.g., a human) and used to measure the concentration of an analyte (e.g., glucose or oxygen) in a medium (e.g., interstitial fluid (ISF) or blood) within the living animal. The sensor may include a light source (e.g., a light-emitting diode (LED) or other light emitting element), indicator molecules in a graft, and a photodetector (e.g., a photodiode, phototransistor, photoresistor or other photosensitive element). Examples of implantable sensors employing indicator molecules to measure the concentration of an analyte are described in U.S. Pat. No. 6,330,464, which is incorporated herein by reference in its entirety.

The sensor may include indicator molecules embedded in an opaque polymer graft (i.e., layer or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether or not glucose is bound to the indicator molecule.

A light source (e.g., light emitting diode (LED)) may emit the excitation light, which may then be absorbed by the indicator molecules in the polymer graft. A portion of the absorbed excitation light may be reflected from the polymer graft back into the sensor, and a portion of the absorbed excitation light may be emitted by the indicator molecules at a higher wavelength. The reflected and emitted light (e.g., fluorescent light) may be absorbed by one or more photodetectors within the body of the sensor.

Error may be introduced into analyte readings taken by a sensor as conditions of the sensor change over the life of the sensor and/or conditions or the sensing medium (e.g., protein concentrations in interstitial fluid) change over time. Thus, there is presently a need in the art for improvements to reduce the introduction of error into analyte readings taken by an implanted sensor.

SUMMARY

The present invention overcomes the disadvantages of prior systems by providing, among other advantages, reduced variation in the opacity of the polymer graft of a sensor that may result from changes in the sensing medium.

One aspect of the present invention provides a sensor that may be for placement within a living animal and for measurement of an analyte in a medium within the living animal. The sensor may include a sensor housing and a polymer graft covering at least a portion of the sensor housing. The polymer graft may include indicator molecules. The opacity of the graft may remain the same over time.

In some embodiments, the polymer graft may be configured to pass a percentage of light and may be configured such that the percentage of light passing through the polymer graft would not change by more than 50% if the sensor were placed within the living animal for at least one month. In some embodiments, the percentage of light passing through the polymer graft may not change by more than 20% if the sensor were placed within the living animal for at least one month. In some embodiments, the percentage of light passing through the polymer graft may not change by more than 10% if the sensor were placed within the living animal for at least one month.

In some embodiments, the percentage of light passing through the polymer graft may not change by more than 50% if the sensor were placed within the living animal for at least two months. In some embodiments, the percentage of light passing through the polymer graft may not change by more than 50% if the sensor were placed within the living animal for at least six months.

Another aspect of the present invention provides a sensor that may be for placement within a living animal and for measurement of an analyte in a medium within the living animal. The sensor may include a sensor housing, polymer graft, light source, and photodetector. The polymer graft may cover at least a portion of the sensor housing. The polymer graft may include indicator molecules. The light source may be configured to emit excitation light to the indicator molecules of the polymer graft. The photodetector may be configured to receive emission light from the indicator molecules of the polymer graft and output a measurement signal indicative of the amount of the received emission light. The amount of the emission light received by the photodetector may be indicative of the amount of the analyte in the medium within the living animal. The polymer graft may be configured such that variation of the opacity of the polymer graft during measurement of the analye in the medium within the living animal causes a change, which is unrelated to the amount of analyte in the medium, in the measurement signal of 20% or less.

In some embodiments, the change in the measurement signal caused by the variation of the opacity of the polymer graft may be 10% or less. In some embodiments, the change in the measurement signal caused by the variation of the opacity of the polymer graft may be 5% or less. In some embodiments, the change in the measurement signal caused by the variation of the opacity of the polymer graft may be 2% or less. In some embodiments, the change in the measurement signal caused by the variation of the opacity of the polymer graft is 1% or less.

In some embodiments, the polymer graft may be clear. In some embodiments, the polymer graft may be opaque. The polymer graft may be a polymer hydrogel including acrylic acid. The polymer graft may be made of a polymer hydrogel including polyethylene glycol (PEG). The polymer graft may be made of a polymer hydrogel including acrylic acid and PEG.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
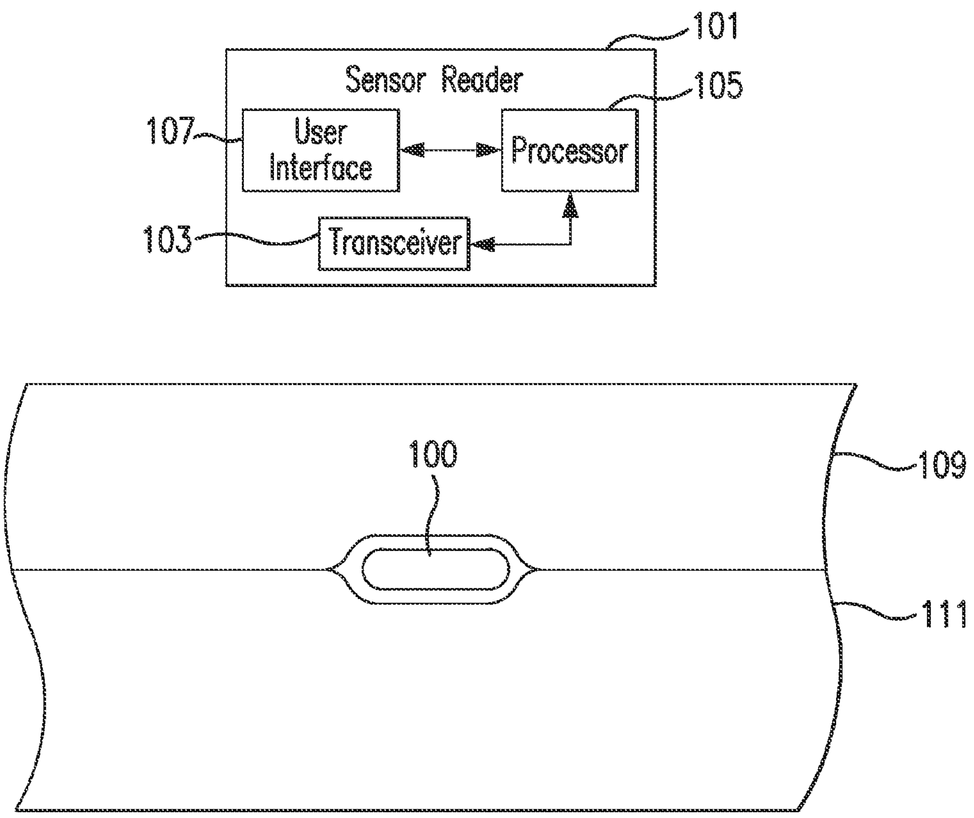
FIG. 1 is a schematic view of a sensor system, which includes an implantable sensor and a sensor reader, embodying aspects of the present invention.
Figure 2:
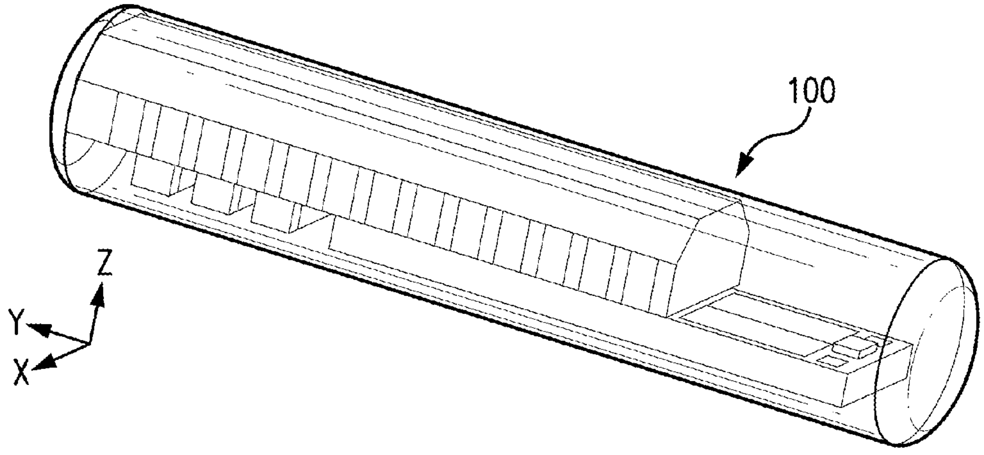
FIG. 2 illustrates a perspective view of a sensor embodying aspects of the present invention.

FIG. 1 is a schematic view of a sensor system embodying aspects of the present invention. In one non-limiting embodiment, the system includes a sensor 100 and an external sensor reader 101. In the embodiment shown in FIG. 1, the sensor 100 is implanted in a living animal (e.g., a living human). The sensor 100 may be implanted, for example, in a living animal's arm, wrist, leg, abdomen, or other region of the living animal suitable for sensor implantation. For example, as shown in FIG. 1, in one non-limiting embodiment, the sensor 100 may be implanted between the skin 109 and subcutaneous tissues 111. In some embodiments, the sensor 100 may be an optical sensor. In some embodiments, the sensor 100 may be a chemical or biochemical sensor.

A sensor reader 101 may be an electronic device that communicates with the sensor 100 to power the sensor 100 and/or obtain analyte (e.g., glucose) readings from the sensor 100. In non-limiting embodiments, the reader 101 may be a handheld reader, a wristwatch, or an armband, for example. In one embodiment, positioning (i.e., hovering or swiping/waiving/passing) the reader 101 within range over the sensor implant site (i.e., within proximity of the sensor 100) will cause the reader 101 to automatically convey a measurement command to the sensor 100 and receive a reading from the sensor 100.

In some embodiments, the sensor reader 101 may include a transceiver 103, a processor 105 and/or a user interface 107. In one non-limiting embodiment, the user interface 107 may include a liquid crystal display (LCD), but, in other embodiments, different types of displays may be used. In some embodiments, the transceiver 103 may include an inductive element, such as, for example, a coil. The transceiver 103 may generate an electromagnetic wave or electrodynamic field (e.g., by using a coil) to induce a current in an inductive element (e.g., inductive element 114 of FIGS. 3-8) of the sensor 100, which powers the sensor 100. The transceiver 103 may also convey data (e.g., commands) to the sensor 100. For example, in a non-limiting embodiment, the transceiver 103 may convey data by modulating the electromagnetic wave used to power the sensor 100 (e.g., by modulating the current flowing through a coil of the transceiver 103). The modulation in the electromagnetic wave generated by the reader 101 may be detected/extracted by the sensor 100. Moreover, the transceiver 103 may receive data (e.g., measurement information) from the sensor 100. For example, in a non-limiting embodiment, the transceiver 103 may receive data by detecting modulations in the electromagnetic wave generated by the sensor 100, e.g., by detecting modulations in the current flowing through the coil of the transceiver 103.

The inductive element of the transceiver 103 and the inductive element (e.g., inductive element 114 of FIGS. 3-8) of the sensor 100 may be in any configuration that permits adequate field strength to be achieved when the two inductive elements are brought within adequate physical proximity. In certain embodiments, the inductive element 114 may be a ferrite hybrid substrate or antenna.

FIGS. 2-8 illustrate a non-limiting embodiment of a sensor 100 embodying aspects of the present invention that may be used in the sensor system illustrated in FIG. 1. In some embodiments, the sensor 100 may be an optical sensor. In one non-limiting embodiment, sensor 100 includes a sensor housing 102 (i.e., body, shell, or capsule). In exemplary embodiments, sensor housing 102 may be formed from a suitable, optically transmissive polymer material, such as, for example, acrylic polymers (e.g., polymethylmethacrylate (PMMA)). The sensor 100 may also include an end cap 113. In some embodiments, the end cap 113 may be formed from a suitable, optically transmissive polymer material, such as, for example, acrylic polymers (e.g., polymethylmethacrylate (PMMA)).

Figure 8:
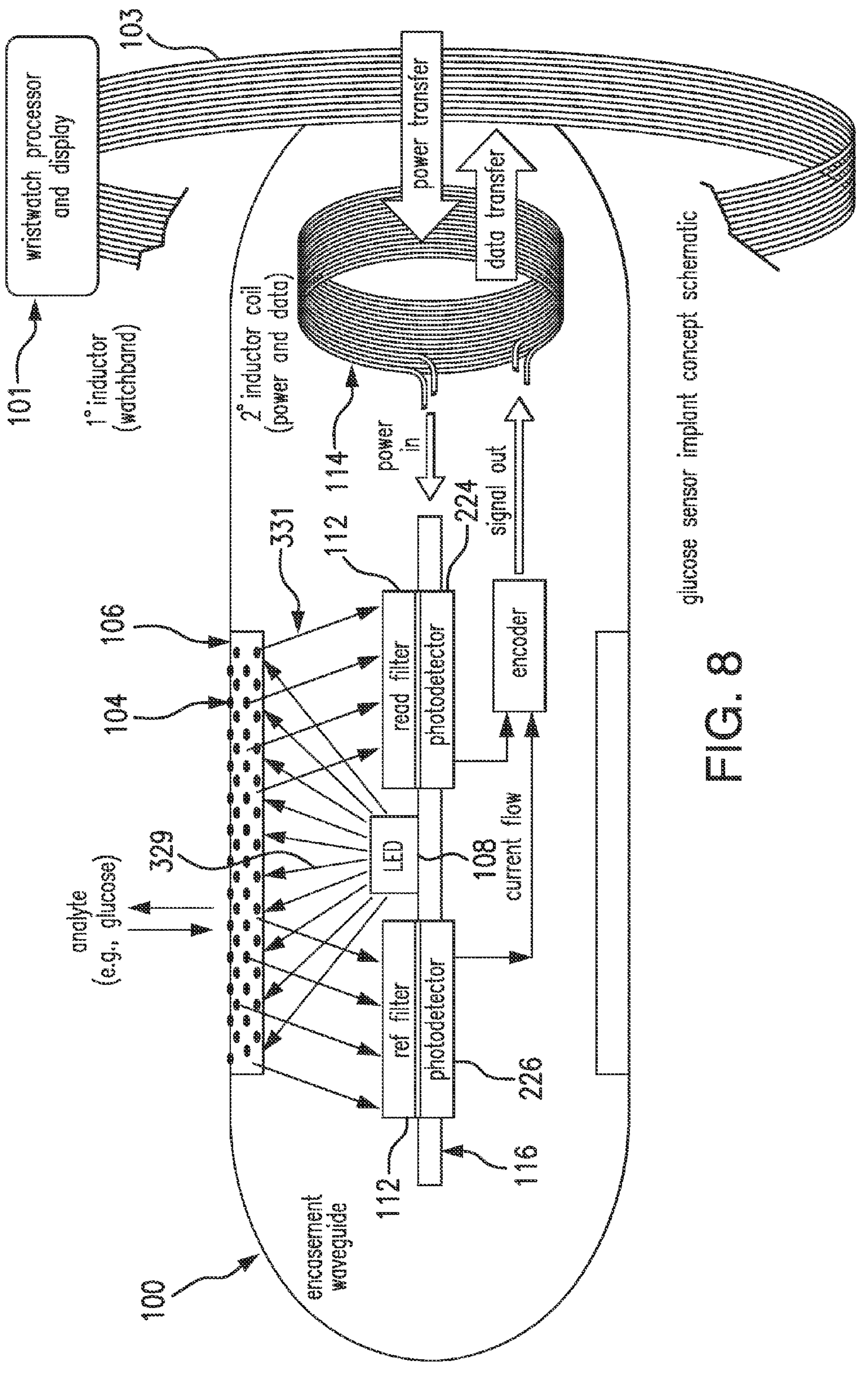
FIG. 8 illustrates a cross-sectional side view of a sensor in operation in accordance with an embodiment of the present invention.

In some embodiments, the sensor 100 includes indicator molecules 104 (see, e.g., FIG. 8). Indicator molecules 104 may be fluorescent indicator molecules (e.g., Trifluoromethylindicator (TFM) fluorescent indicator molecules having the chemical name 9-[N-[6-(4,4,5,5-tetramethyl-1,3,2-dioxaborolano)-3-(trifluoromethyl)benzyl]-N-[3-(methacrylamido)propylamino]methyl]-10-[N-[6-(4,4,5,5-tetramethyl-1,3,2-dioxaborolano)-3-(trifluoromethyl)benzyl]-N-[2-(carboxyethyl)amino]methyl]anthracene sodium salt) or absorption indicator molecules. In some embodiments, the indicator molecules 104 may reversibly bind an analyte (e.g., glucose or oxygen). When an indicator molecule 104 has bound an analyte, the indicator molecule may become fluorescent, in which case the indicator molecule 104 is capable of absorbing (or being excited by) excitation light 329 and emitting light 331, as illustrated in FIG. 8. In one non-limiting embodiment, the excitation light 329 may have a wavelength of approximately 378 nm, and the emission light 331 may have a wavelength in the range of 400 to 500 nm. When no analyte is bound, the indicator molecule 104 may be only weakly fluorescent.

In some non-limiting embodiments, sensor 100 may include a polymer graft 106 (i.e., matrix layer or hydrogel) coated or embedded on at least a portion of the exterior surface of the sensor housing 102, with the indicator molecules 104 distributed throughout the polymer graft 106. The polymer graft 106 may cover the entire surface of sensor housing 102 or only one or more portions of the surface of housing 102. Similarly, the indicator molecules 104 may be distributed throughout the entire graft 106 or only throughout one or more portions of the graft 106. Furthermore, as an alternative to coating the graft 106 on the outer surface of sensor housing 102, the graft 106 may be disposed on the outer surface of the sensor housing 102 in other ways, such as by deposition or adhesion.

In the illustrated embodiment, the sensor 100 includes a light source 108, which may be, for example, a light emitting diode (LED) or other light source, that emits radiation, including radiation over a range of wavelengths that interact with the indicator molecules 104.

In the illustrated embodiment, sensor 100 also includes one or more photodetectors 110 (e.g., photodiodes, phototransistors, photoresistors or other photosensitive elements) which, in the case of a fluorescence-based sensor, is sensitive to fluorescent light emitted by the indicator molecules 104 such that a signal is generated by the photodetector 110 in response thereto that is indicative of the level of fluorescence of the indicator molecules and, thus, the amount of analyte of interest (e.g., glucose).

As illustrated in FIG. 8, some embodiments of sensor 100 include one or more optical filters 112, such as high pass or band pass filters, that may cover a photosensitive side of the one or more photodetectors 110.

As shown in FIG. 8, in some embodiments, sensor 100 may be wholly self-contained. In other words, the sensor may be constructed in such a way that no electrical leads extend into or out of the sensor housing 102 to supply power to the sensor (e.g., for driving the light source 108) or to convey signals from the sensor 100. Instead, in one embodiment, sensor 100 may be powered by an external power source (e.g., external sensor reader 101). For example, the external power source may generate a magnetic field to induce a current in an inductive element 114 (e.g., a coil or other inductive element). Additionally, the sensor 100 may use the inductive element 114 to communicate information to an external sensor reader (e.g., sensor reader 101). In some embodiments, the external power source and data reader may be the same device.

In some embodiments, sensor 100 may include a substrate 116. The substrate 116 may be a circuit board (e.g., a printed circuit board (PCB)) on which circuit components (e.g., analog and/or digital circuit components) may be mounted or otherwise attached. However, as an alternative, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components. Circuitry of the sensor 100 may incorporate some or all of the structure described in U.S. patent application Ser. No. 13/650,016, which is incorporated herein by reference in its entirety, with particular reference to FIG. 11D or U.S. patent application Ser. No. 13/761,839, which is incorporated herein by reference in its entirety, with particular reference to FIG. 6.

In some embodiments, the one or more photodetectors 110 may be mounted on the semiconductor substrate 116, but, in some preferred embodiments, the one or more photodetectors 110 may be fabricated in the semiconductor substrate 116. In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

In some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116. In certain embodiments, the one or more capacitors 118 may be one or more antenna tuning and decoupling capacitors.

In some embodiments, the sensor 100 may include a reflector 119 (i.e., mirror). Reflector 119 may be attached to the semiconductor substrate 116 at an end thereof (see, FIG. 3). In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from entering the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

The specific composition of the polymer graft 106 and the indicator molecules 104 may vary depending on the particular analyte the sensor is to be used to detect and/or where the sensor is to be used to detect the analyte (i.e., in the blood or in subcutaneous tissues). Preferably, however, graft 106 should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

Figure 4:
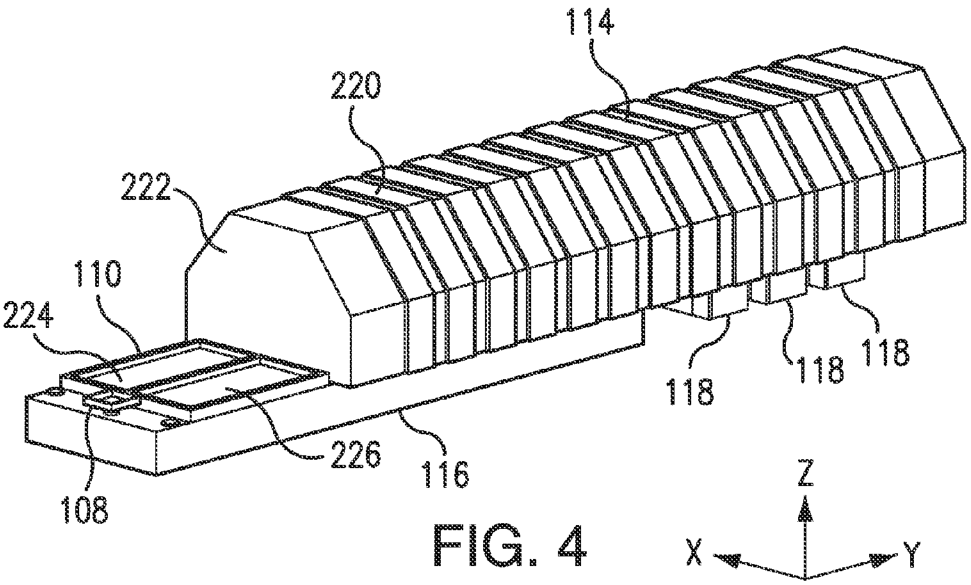
FIGS. 4 and 5 illustrate perspective views of sensor components within the sensor body/shell/capsule of a sensor embodying aspects of the present invention.
Figure 5:
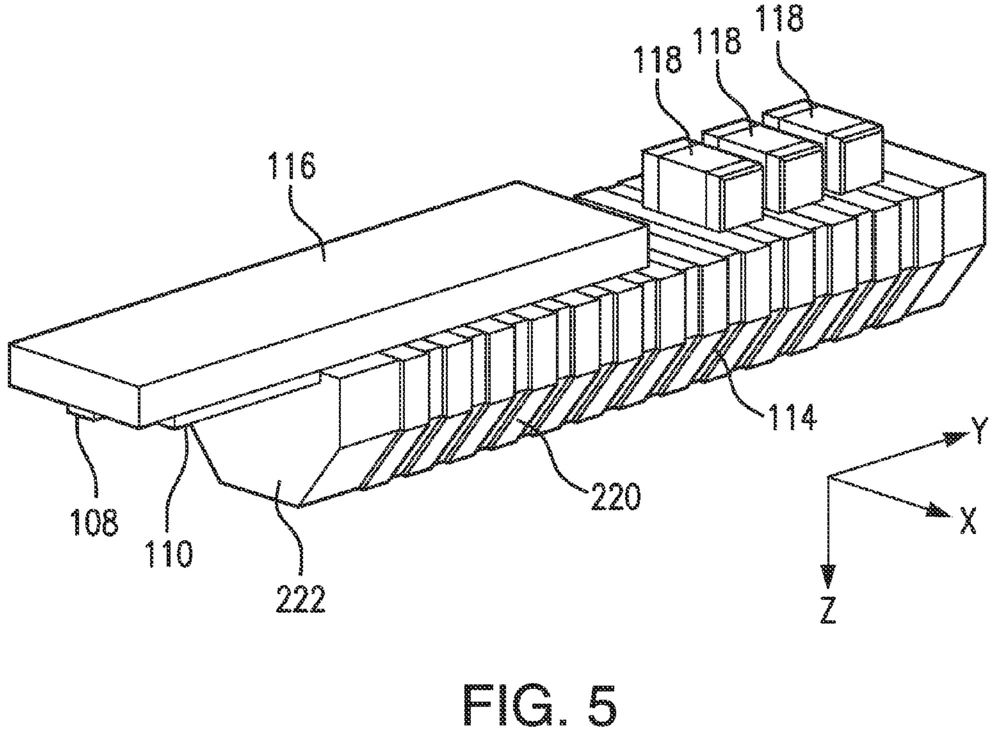

FIGS. 4 and 5 illustrate perspective views of the sensor 100. In FIGS. 4 and 5, the sensor housing 102, filters 112, and the reflector 119, which may be included in some embodiments of the sensor 100, are not illustrated. As shown in the illustrated embodiment, the inductive element 114 may comprise a coil 220. In one embodiment, coil 220 may be a copper coil but other conductive materials, such as, for example, screen printed gold, may alternatively be used. In some embodiments, the coil 220 is formed around a ferrite core 222. Although core 222 is ferrite in some embodiments, in other embodiments, other core materials may alternatively be used. In some embodiments, coil 220 is not formed around a core. Although coil 220 is illustrated as a cylindrical coil in FIGS. 4 and 5, in other embodiments, coil 220 may be a different type of coil, such as, for example, a flat coil.

In some embodiments, coil 220 is formed on ferrite core 222 by printing the coil 220 around the ferrite core 222 such that the major axis of the coil 220 (magnetically) is parallel to the longitudinal axis of the ferrite core 222. A non-limiting example of a coil printed on a ferrite core is described in U.S. Pat. No. 7,800,078, which is incorporated herein by reference in its entirety. In an alternative embodiment, coil 220 may be a wire-wound coil. However, embodiments in which coil 220 is a printed coil as opposed to a wire-wound coil are preferred because each wire-wound coil is slightly different in characteristics due to manufacturing tolerances, and it may be necessary to individually tune each sensor that uses a wire-wound coil to properly match the frequency of operation with the associated antenna. Printed coils, by contrast, may be manufactured using automated techniques that provide a high degree of reproducibility and homogeneity in physical characteristics, as well as reliability, which is important for implant applications, and increases cost-effectiveness in manufacturing.

In some embodiments, a dielectric layer may be printed on top of the coil 220. The dielectric layer may be, in a non-limiting embodiment, a glass based insulator that is screen printed and fired onto the coil 220. In an exemplary embodiment, the one or more capacitors 118 and the semiconductor substrate 116 may be mounted on vias through the dielectric.

In the illustrated embodiment, the one or more photodetectors 110 include a first photodetector 224 and a second photodetector 226. First and second photodetectors 224 and 226 may be mounted on or fabricated in the semiconductor substrate 116.

Figure 6:
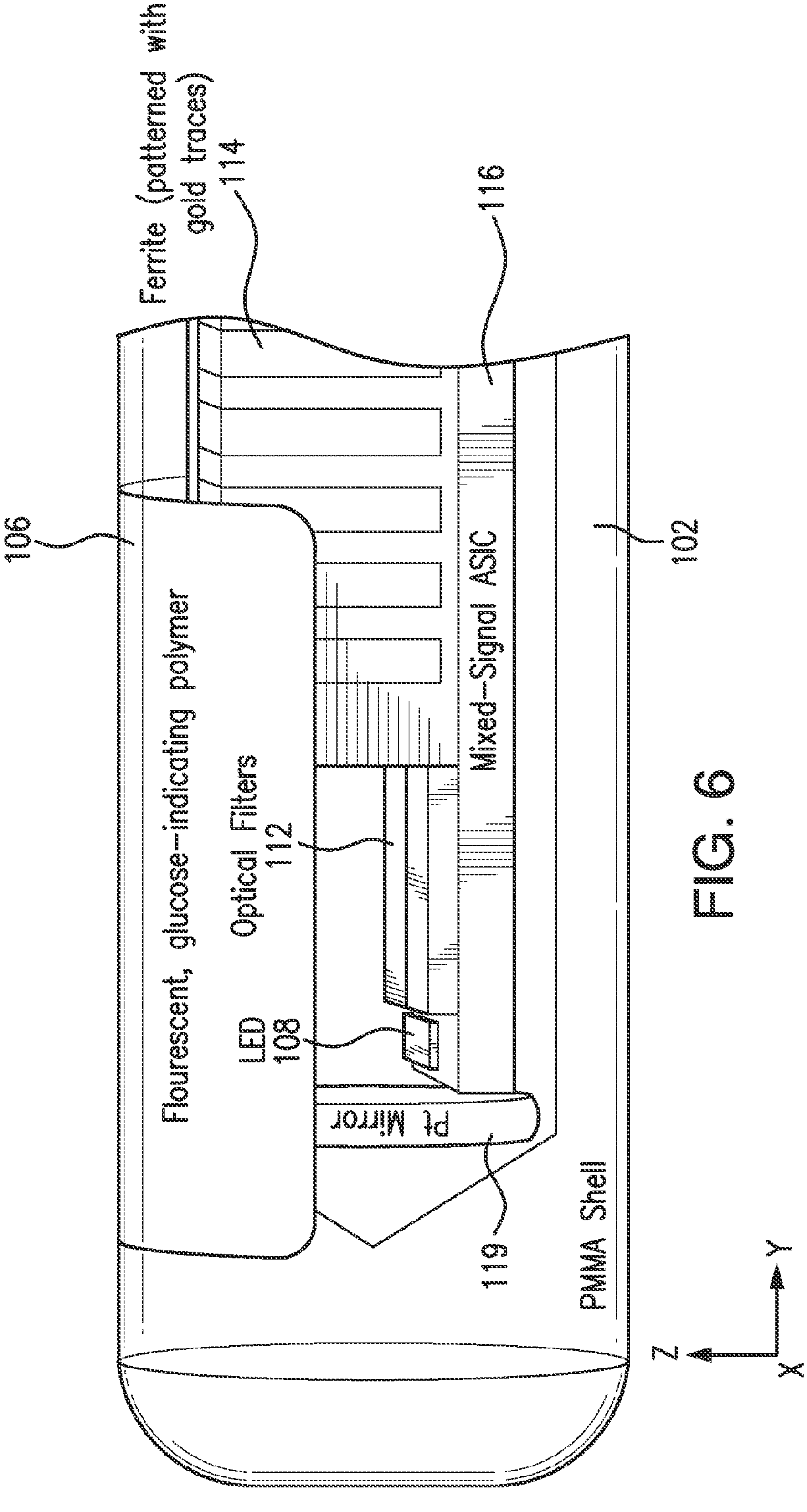
FIG. 6 illustrates a side view of a sensor embodying aspects of the present invention.
Figure 7:
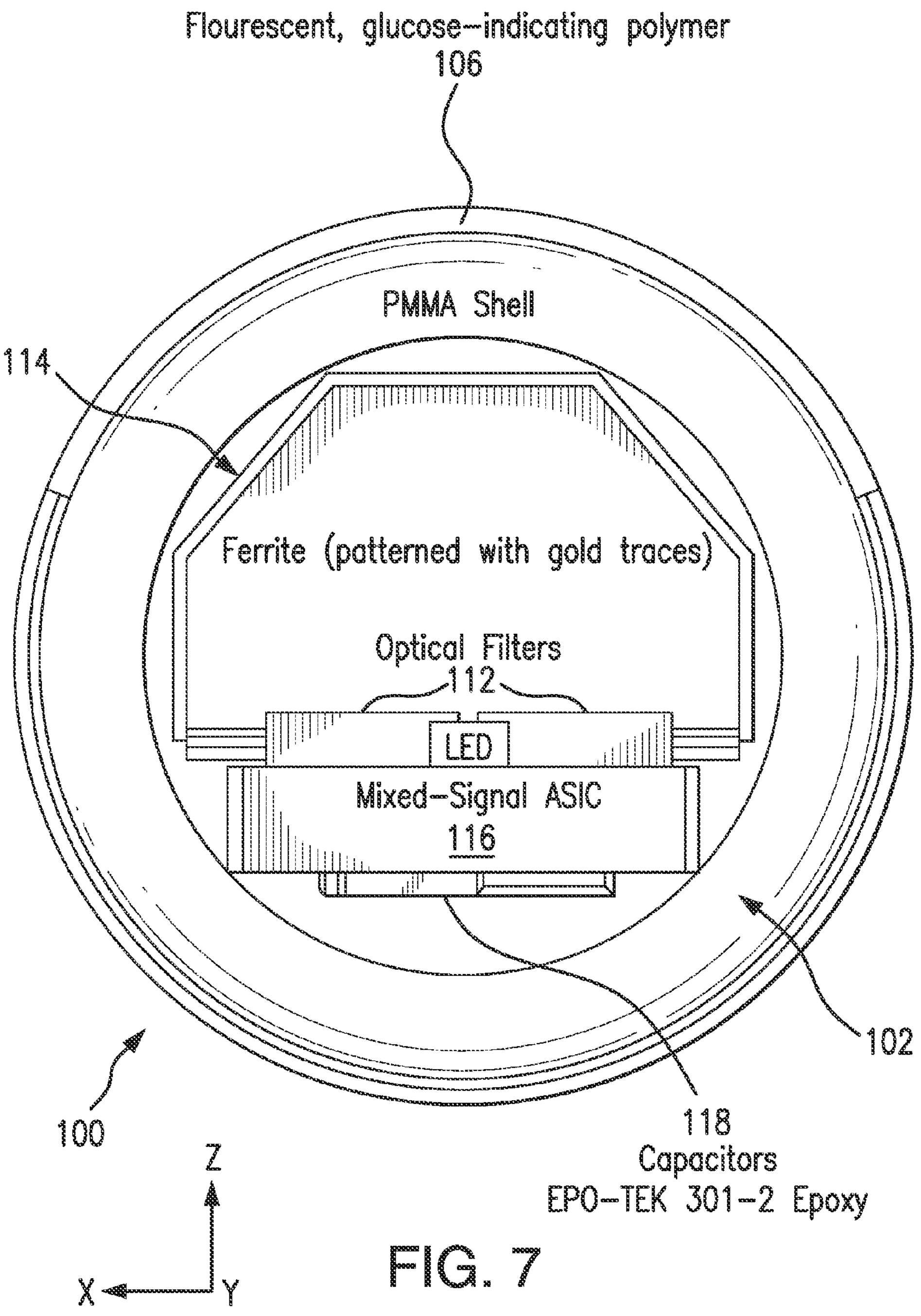
FIG. 7 illustrates a cross-sectional end view of a sensor embodying aspects of the present invention.

FIGS. 6 and 7 illustrate side and cross-sectional views, respectively, of the sensor 100 according to one embodiment. As illustrated in FIGS. 6 and 7, the light source 108 may be positioned to emit light that travels within the sensor housing 102 and reaches the indicator molecules 104 of the polymer graft 106, and the photodetectors 110, which may be located beneath filters 112, may be positioned to receive light from the indicator molecules 104 of the polymer graft 106.

In operation, as shown in FIG. 8, the light source 108 (e.g., an LED) may emit excitation light 329 that travels within the sensor housing 102 and reaches the indicator molecules 104 of the polymer graft 106. In a non-limiting embodiment, the excitation light 329 may cause the indicator molecules 104 distributed in graft 106 to fluoresce. As the graft 106 may be permeable to the analyte (e.g., glucose) in the medium (e.g., ISF) into which the sensor 100 is implanted, the indicator molecules 104 in the graft 106 may interact with the analyte in the medium and, when irradiated by the excitation light 329, may emit indicator fluorescent light 331 indicative of the presence and/or concentration of the analyte in the medium.

Figure 3:
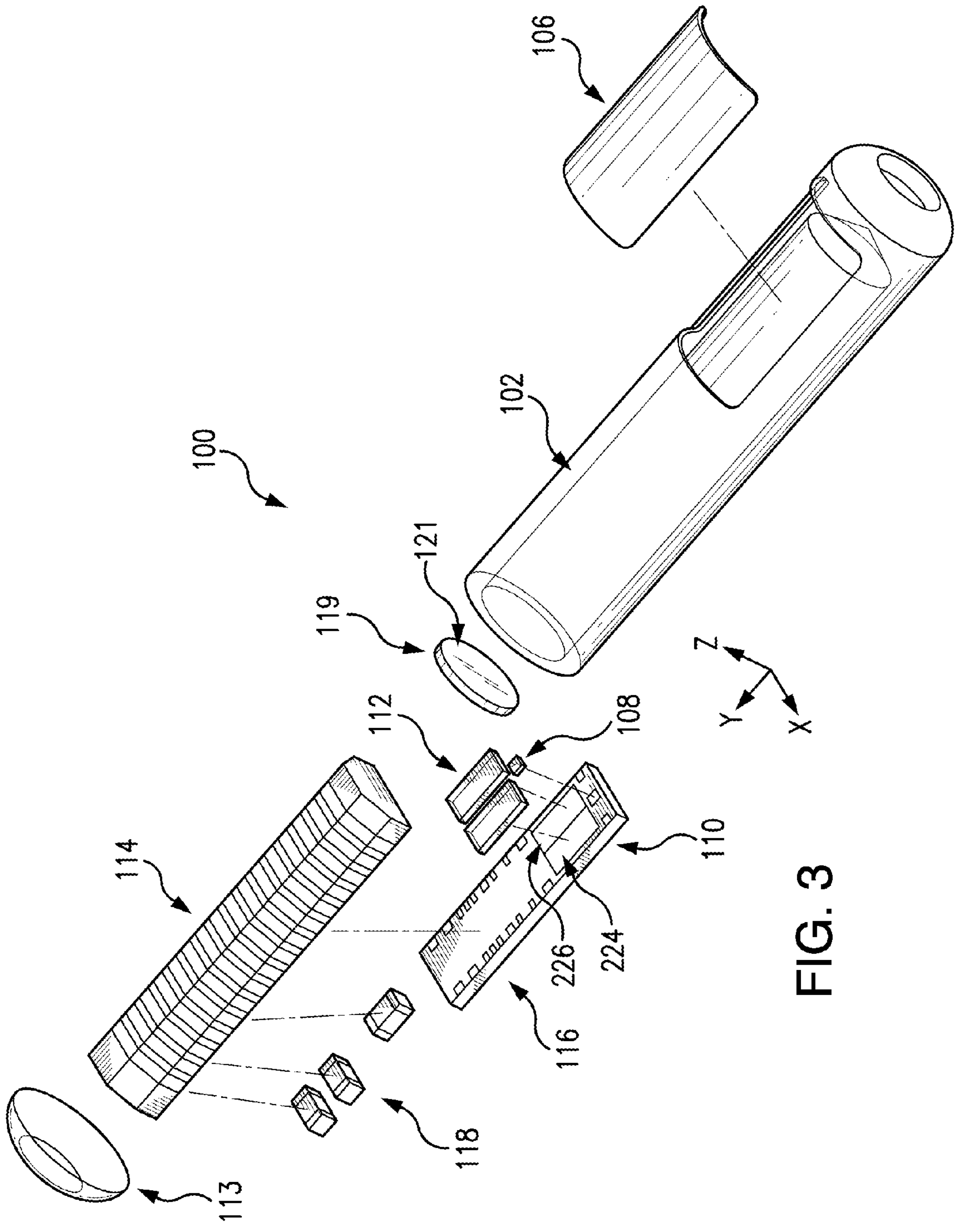
FIG. 3 illustrates an exploded view of a sensor embodying aspects of the present invention.

The photodetectors 224 and 226 are used to receive light (see FIG. 3). Each photodetector 224 and 226 may be covered by a filter 112 that allows only a certain subset of wavelengths of light to pass through (see FIG. 3). In non-limiting embodiments, the filters 112 may be thin film (e.g., dichroic) filters, and may be deposited on glass or other substrates. The filters 112 may pass only a narrow band of wavelengths and otherwise reflect the received light.

Photodetector 226 may be a reference photodetector, and the reference filter 112 (i.e., the filter 112 covering photodetector 226) may pass light at the same wavelength as the wavelength of the excitation light 329 emitted from the light source 108 (e.g., 378 nm). However, this is not required, and, in alternative embodiments, the reference filter 112 may pass light at a different wavelength (e.g., the wavelength of light emitted by reference indicator molecules having optical characteristics not affected or substantially not affected by the presence of the analyte in the medium).

Photodetector 224 may be a signal photodetector that detects the amount of fluorescent light 331 that is emitted from the indicator molecules 104 in the polymer graft 106. In some non-limiting embodiments, the signal filter 112 (i.e., the filter 112 covering photodetector 224) may pass light in the range of about 400 nm to 500 nm. Higher glucose levels correspond to a greater amount of fluorescence of the molecules 104 in the graft 106, and therefore, a greater amount of photons striking the signal photodetector 224.

Although in some embodiments, as illustrated in FIGS. 1-8, the analyte sensor 100 may be a fully implantable sensor, this is not required, and, in some alternative embodiments, the sensor 100 may be a transcutaneous sensor having a wired connection to the sensor reader 101. For example, in some alternative embodiments, the sensor 100 may be located in or on a transcutaneous needle (e.g., at the tip thereof). In these embodiments, instead of wirelessly communicating using inductive element 114 and transceiver 103, the sensor 100 and sensor reader 101 may communicate using one or more wires connected between the sensor reader 101 and the transcutaneous needle that includes the sensor 100. For another example, in some alternative embodiments, the sensor 100 may be located in a catheter (e.g., for intravenous blood glucose monitoring) and may communicate (wirelessly or using wires) with the sensor reader 101. Thus, a sensor 100 placed within a living animal may or may not be an implanted sensor.

The applicants have found, through repeated testing, that the opacity of an opaque polymer graft (e.g., a polymer graph that is translucent and/or cloudy) tends to vary during the time the sensor is placed within the living animal. This variation in the opacity may be caused by changes in the composition of the medium (e.g., interstitial fluid) around the sensor 100. These changes may be, for example, changes in protein concentration, fat concentration, temperature, volume, and/or number of cells in the medium. The variation in the opacity may be, for example, dynamic—from analyte measurement to analyte measurement (e.g., minute to minute). The variation in opacity may additionally or alternatively be dynamic over time (e.g., from day to day).

Variation in the opacity of an opaque polymer graft may disrupt analyte readings. In particular, when a polymer graft is opaque (i.e., cloudy), excitation light 329 emitted from the light source 108 in the sensor 100 may reflect off of the polymer graft/hydrogel and may be absorbed by the one or more photodetectors 110. As the opacity varies and the polymer graft/hydrogel becomes less opaque (i.e., more clear), more excitation light 329 may pass through the polymer graft/hydrogel. As a result, less excitation light 329 may be reflected off the polymer graft/hydrogel and onto the one or more photodetectors 110. Further, less fluorescent light 331 may also be reflected off the polymer graft and absorbed by one or more of the photodetectors 110. Thus, the variation in the opacity may cause a change in the output of the one or more photodetectors 110, and this change may be unrelated to the amount of analyte in the medium.

Error may be introduced in the analyte readings as the opacity of the polymer graft/hydrogel changes. When opacity is at an increased level, there may be an increase in the amount of excitation light 329 or fluorescent light 331 absorbed into the polymer graft/hydrogel and then reflected back into the one or more photodetectors 110. However, when the hydrogel is less opaque and clearer in nature, there may be a decrease in the amount of excitation light 329 or fluorescent light 331 absorbed by the one or more photodetectors 110. When the polymer graft/hydrogel is opaque, there may be no way to distinguish whether a higher analyte reading is due to (a) more light being absorbed by the photodiodes because of opacity or (b) an actual increase in concentration of the analyte (e.g., glucose) in the medium (e.g., ISF).

Accordingly, in some embodiments, the polymer graft 106 may be configured to have little or no variation in opacity during the time in which the sensor 100 is placed within the living animal (e.g., with protein infiltration) and, thus, may reduce the corresponding error in analyte readings. In other words, in some embodiments, because the variation of the polymer graft 106 is reduced, the change in the photodetector output caused by the opacity variation may be reduced. In some non-limiting embodiments, the sensor 100 may be configured to be placed within the living animal for at least one day, one week, two weeks, one month, two months, six months, one year, or longer. In some non-limiting embodiments, the polymer graft 106 may be configured to pass a percentage of light (e.g., 70%) and may be configured such that the percentage of light allowed to pass through the polymer graft 106 does not change by more than a certain percentage (e.g., 50%, 30%, 20%, 10%, 5%, 2%, or 1%) for at least the duration of the time for which the sensor 100 is configured to be placed within the living animal (e.g., one day, one week, two weeks, one month, two months, three months, six months, one year, or longer). In some embodiments, the polymer graft 106 may be clear. In some alternative embodiments, the polymer graft 106 may be opaque (i.e., translucent and/or cloudy).

In some embodiments, the polymer graft 106 may be configured such that variation of the opacity of the polymer graft during measurement of the analye in the medium within the living animal is small or non-existent. As a result, the variation in the opacity may cause not more than a small change, which is unrelated to the amount of analyte in the medium, in the measurement signal output by a photodetector (e.g., photodetector 224). In some non-limiting embodiments, the change in the measurement signal caused by the variation of the opacity of the polymer graft 106 may be, for example, 20% or less, 15% or less, 10% or less, 5% or less, 2% or less, 1% or less, or 0.5% or less.

In some non-limiting embodiments, the percentage of light allowed to pass through the polymer graft 106 does not change by more than a percentage within a range of 0% to 50%, and this range of percentages should be understood as describing and disclosing all percentages (including all decimal or fractional percentage numbers) within this range. In some non-limiting embodiments, variation in the opacity of the polymer graft 106 does not cause a change in a measurement signal output by a photodetector of more than a percentage within a range of 0% to 20%, and this range of percentages should be understood as describing and disclosing all percentages (including all decimal or fractional percentage numbers) within this range.

In some embodiments, the polymer graft 106 has acceptably fast analyte response time and an acceptable analyte responsivity. Analyte response time is the amount of time needed for the indicator molecules 104 in the polymer graft 106 to respond (e.g., change an optical characteristic) to a change in glucose concentration. Whether an analyte response time is acceptably fast is use dependent. For example, in the context of a polymer graft in a sensor placed in a human and used for in vivo measurement of changes in glucose concentration in interstitial fluid, an analyte response time may be acceptably fast when fast enough to detect a hypoglycemic or hyperglycemic event and allow time for the human to respond appropriately. In some embodiments, the polymer graft 106 may have an analyte response time less than 15 minutes. In one non-limiting embodiment, the polymer graft 106 may have an analyte response time of less than 10 minutes. In another non-limiting embodiment, the polymer graft 106 may have an analyte response time of less than 5 minutes.

Analyte responsivity is the degree to which indicator molecules 104 in the polymer graft 106 respond (e.g., change an optical characteristic) to a change in glucose concentration. Analyte responsivity may be acceptable when the response produces a measurable change (e.g., when a change in the amount of light 331 emitted by the indicator molecules 104 of the polymer graft 106 is sufficient to measurably change the signal output by the signal photodetector 224).

In one non-limiting embodiment, the polymer graft 106 may contain three monomers: (i) the TFM fluorescent indicator, (ii) hydroxyethylmethacrylate (HEMA), which is a methacrylate, and (iii) polyethylene glycol (PEG). In some embodiments, the PEG may be polyethylene glycol methacrylate (PEG-methacrylate) or polyethylene glycol diacrylate (PEG-diacrylate or PEGDA). The three monomers may be in specific molar ratios. For an example of an opaque polymer graft, in a non-limiting embodiment, the fluorescent indicator may comprise 0.1 molar percent, HEMA may comprise 94.3 molar percent, and PEGDA may comprise 5.6 molar percent. With this formulation, the combined (i.e., total) monomers may, in one example, be 30% by volume of the polymerization solution used for the polymerization reaction with the remainder of the polymerization solution being water (i.e., the polymerization solution may be 70% water by volume). For another example, in one non-limiting embodiment, the polymer graft 106 may be made using a polymer solution that is 50% water by volume and 50% monomers by volume, where the TFM fluorescent indicator, HEMA, and PEGDA may comprise 0.1 molar percent, 94.1 molar percent, and 5.8 molar percent, respectively, of the monomers in the solution.

The PEGDA may act as a cross-linker and create a sponge-like matrix/hydrogel. In some non-limiting embodiments, the PEG-containing graft/hydrogel may become clear if a sufficient amount of additional PEG is added to the mixture (i.e., if it is fabricated with a higher concentration of PEG), and a clear polymer graft 106 may be made from such a formulation. For example, in one non-limiting embodiment, the polymer graft 106 may be made using a polymer solution that is 50-60% water by volume and 40-50% monomers by volume, where the TFM fluorescent indicator, HEMA, and PEG-methacrylate may comprise 0.1 molar percent, 49.9 molar percent, and 50 molar percent, respectively, of the monomers in the solution. In some embodiments, the polymer graft may be synthesized using conventional free radical polymerization.

In some alternative embodiments, a clear polymer graft 106 may be made by substituting acrylic acid for the PEG. With low concentrations of acrylic acid, this composition may be opaque, and the opacity may vary over time. However, similar to PEG, at higher concentrations of acrylic acid, the polymer graft/hydrogel becomes clear. For example, in one non-limiting embodiment, the polymer graft 106 may be made using a polymer solution that is 55% water by volume and 45% monomers by volume, where the fluorescent indicator, HEMA, PEGDA, and acrylic acid may comprise 0.1 molar percent, 81.8 molar percent, 0.1 molar percent, and 18 molar percent, respectively, of the monomers in the solution. In some embodiments, a polymer graft

106 made with acrylic acid may have mechanical properties superior to a polymer graft not made with acrylic acid. For example, in one non-limiting embodiment, the polymer graft 106 made with acrylic acid may be less brittle and may remain elastic.

In some other alternative embodiments, a clear polymer graft 106 may be formed using relatively high total concentrations of both acrylic acid and PEG. For example, in one non-limiting embodiment, the polymer graft 106 may be made using a polymer solution that is 50% water by volume and 50% monomers by volume, where the fluorescent indicator, HEMA, PEGDA, and acrylic acid may comprise 0.1 molar percent, 79.45 molar percent, 2.45 molar percent, and 18 molar percent, respectively, of the monomers in the solution. For another example, in one non-limiting embodiment, the polymer graft 106 may be made using a polymer solution that is 50% water by volume and 50% monomers by volume, where the fluorescent indicator, HEMA, PEGDA, and acrylic acid may comprise 0.1 molar percent, 83.68 molar percent, 2.45 molar percent, and 13.77 molar percent, respectively, of the monomers in the solution. By incorporating a higher percentage of acrylic acid instead of (or in addition to) PEG, the graft 106 may be much less opaque, and the opacity may not change over time. This may improve accuracy in measurements of analyte concentrations as changes in opacity affect the readings. In embodiments that use acrylic acid to form the polymer graft 106, opacity may not change and analyte readings may be unaffected.

Figure 10:
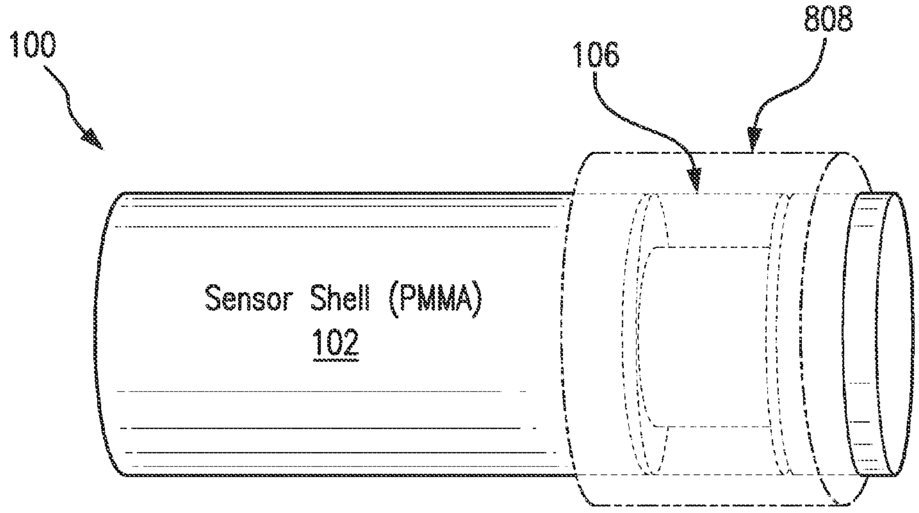

In embodiments having a polymer graft/hydrogel 106 that is clear, light may pass through polymer graft 106 and may be reflected back to the photodetector(s) 110 of sensor 100 from tissue outside the sensor 100, creating noise. Accordingly, in some embodiments, as illustrated in FIG. 10, an opaque analyte permeable membrane 808 may be used to (i) block light from passing beyond the graft 106 and (ii) channel analyte (e.g., glucose) to the graft 106. In other words, in some embodiments, an analyte permeable membrane 808 may be used to cover the clear polymer graft 106 of the sensor 100 and to allow light to reflect off of the analyte permeable membrane 808 rather than passing through the graft 106 and reflecting off of tissue.

Figure 9:
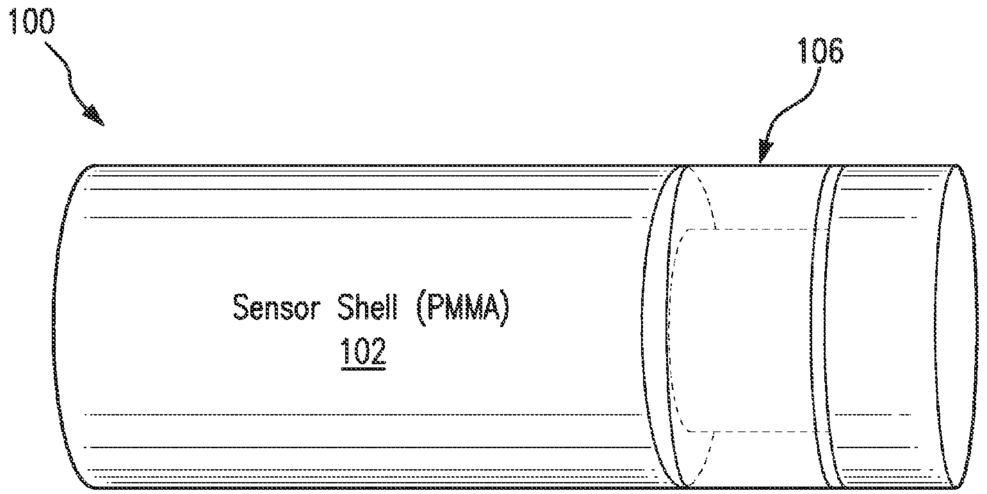
FIGS. 9 and 10 illustrate a side view of a sensor, without and with an analyte permeable membrane (e.g., nylon) over the graft, respectively, in accordance with an embodiment of the present invention.

FIGS. 9 and 10 illustrate a sensor 100 having an analyte permeable membrane 808 in accordance with an embodiment of the present invention. FIG. 9 shows the sensor 100 without the analyte permeable membrane 808, and FIG. 10 shows the sensor 100 with the analyte permeable membrane 808. In some non-limiting embodiments, the sensor 100 may have a sensor housing/shell 102 and a polymer graft 106 covering at least a portion of the housing 102. The graft 106 may include indicator molecules 104.

In some embodiments, the sensor 100 may have features to prevent or reduce graft deterioration, which may be caused by white blood cells, including neutrophils, that may attack an implanted sensor 100. The neutrophils release, inter alia, hydrogen peroxide or other reactive oxygen species (ROS), which may degrade indicator molecules 104 (e.g., by oxidizing a boronate group of an indicator molecule and disabling the ability of the indicator molecule to bind glucose) in the graft 106.

As illustrated in FIGS. 9 and 10, in some non-limiting embodiments, the graft 106 may have thin layer (e.g., 10 nm) or foil on the outside of the graft 106. The thin layer/foil may protect against indicator molecule degradation. The thin layer may be platinum, and the platinum may be sputtered onto the outside surface of the graft 106, which includes the indicator molecules 104. Platinum rapidly catalyzes the conversion of hydrogen peroxide into water and oxygen, which are harmless to the sensor. The rate of this reaction is much faster than the boronate oxidation; thus, the platinum is effective at protecting the boronate from oxidation by reactive oxygen species. Although platinum is the catalyst of the conversion of hydrogen peroxide into water and oxygen in some embodiments, in alternative embodiments, other catalysts of this reaction, such as, for example, palladium or catalase, may be used for the thin layer/foil instead of or in addition to platinum.

As illustrated in FIG. 10, the sensor 100 may have an analyte permeable membrane 808 over the graft 106 (and over any thin layer/film on the outside of the graft 106). The analyte permeable membrane 808 may be opaque and, therefore, perform a light-blocking function. In other words, the opaque nature of the analyte permeable membrane may serve the function of effectively blocking the extraneous light from the photodetectors 110. In some non-limiting embodiments, the opaque analyte permeable membrane 808 may be physically attached over the polymer graft 106 after boring an additional, smaller well into the capsule/housing 102.

In one non-limiting embodiment, the analyte permeable membrane 808 has small pores (e.g., pores having a pore size of 5 microns or less) that block white blood cells (e.g., neutrophils), which are between 6 and 12 microns in diameter, from reaching the underlying graft 106 to attack it. The small pores, however, would at the same time be large enough to allow the analyte to reach the graft 106. In this way, a porous membrane 808 having small pores would increase sensor longevity while not affecting the ability of the sensor 100 to measure the concentration of an analyte.

In some embodiments, the opaque analyte permeable membrane 808 may be made from a material that does not react adversely to the body's defenses. In non-limiting embodiments, the material from which the opaque analyte permeable membrane 808 is made may additionally be both porous (e.g., to allow an analyte, such as glucose, to flow through it) and opaque (e.g., to prevent light from traveling through it). For example, in some embodiments, the analyte permeable membrane material may be a hydrophilic material or a hydrophobic material that is functionalized (e.g., by derivatization) to make it hydrophilic, such as nylon, cellulose acetate, polypropylene (PP), polyvinyl alcohol (PVA), polybutylene terephthalate (PBT), polyether ether ketone (PEEK), polyanhydride, polyamide, polyvinylchloride (PVC), polyethersulfone (PES), polyethylene terephthalate (PET), polyvinylidene difluoride (PVDF), polytetrafluoroethylene (PTFE), and/or polycarbonate.

In some embodiments, to enhance biocompatibility and/or hydrophilicity, the analyte permeable membrane 808 may comprise an additional thin layer, and/or the analyte permeable membrane 808 may have multiple analyte permeable membrane layers.

When the opacity of the polymer graft 106 remains the same over time, reflection of light back into the photodetector(s) 110 may not fluctuate as often as when opacity changes. Therefore, reflection of light off of the graft 106 and analyte permeable membrane 808 may be based solely on the level of analyte (e.g., glucose) in the medium, not opacity.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, circuitry of the sensor 100 and reader 101 may be implemented in hardware, software, or a combination of hardware and software. The software may be implemented as computer executable instructions that, when executed by a processor, cause the processor to perform one or more functions.

What is claimed is:

1. A sensor for placement within a living animal and for measurement of an analyte in a medium within the living animal, the sensor comprising:

a sensor housing; and a polymer graft including indicator molecules and covering at least a portion of the sensor housing;

wherein the polymer graft is clear, and the opacity of the graft remains the same over time.

2. A sensor for placement within a living animal and for measurement of an analyte in a medium within the living animal, the sensor comprising:

a sensor housing; and a polymer graft including indicator molecules and covering at least a portion of the sensor housing, wherein the polymer graft is clear, configured to pass a percentage of light and configured such that the percentage of light passing through the polymer graft would not change by more than 50% if the sensor were placed within the living animal for at least one month.

3. The sensor of claim 2, wherein the percentage of light passing through the polymer graft would not change by more than 20% if the sensor were placed within the living animal for at least one month.

4. The sensor of claim 3, wherein the percentage of light passing through the polymer graft would not change by more than 10% if the sensor were placed within the living animal for at least one month.

5. The sensor of claim 2, wherein the percentage of light passing through the polymer graft would not change by more than 50% if the sensor were placed within the living animal for at least two months.

6. The sensor of claim 2, wherein the percentage of light passing through the polymer graft would not change by more than 50% if the sensor were placed within the living animal for at least six months.

7. A sensor for placement within a living animal and for measurement of an analyte in a medium within the living animal, the sensor comprising:

a sensor housing; and a polymer graft including indicator molecules, said polymer graft covering at least a portion of the sensor housing;

a light source configured to emit excitation light to the indicator molecules of the polymer graft;

a photodetector configured to receive emission light from the indicator molecules of the polymer graft and output a measurement signal indicative of the amount of the received emission light, wherein the amount of the emission light received by the photodetector is indicative of the amount of the analyte in the medium within the living animal;

wherein the polymer graft is clear and configured such that variation of the opacity of the polymer graft during measurement of the analye in the medium within the living animal causes a change, which is unrelated to the amount of analyte in the medium, in the measurement signal of 20% or less.

8. The sensor of claim 7, wherein the change in the measurement signal caused by the variation of the opacity of the polymer graft is 10% or less.

9. The sensor of claim 8, wherein the change in the measurement signal caused by the variation of the opacity of the polymer graft is 5% or less.

10. The sensor of claim 9, wherein the change in the measurement signal caused by the variation of the opacity of the polymer graft is 2% or less.

11. The sensor of claim 10, wherein the change in the measurement signal caused by the variation of the opacity of the polymer graft is 1% or less.

12. The sensor of claim 7, wherein the polymer graft has an analyte response time less than 15 minutes.

13. The sensor of claim 12, wherein the polymer graft has an analyte response time less than 10 minutes.

14. The sensor of claim 13, wherein the polymer graft has an analyte response time less than 5 minutes.

15. The sensor of claim 7, wherein the polymer graft is made of a polymer hydrogel including acrylic acid.

16. The sensor of claim 15, wherein the polymer hydrogel includes polyethylene glycol monomers.

17. The sensor of claim 7, wherein the polymer graft is made of a polymer hydrogel including polyethylene glycol monomers.

18. The sensor of claim 7, further comprising a layer of platinum on an outside surface of the polymer graft.

19. The sensor of claim 18, wherein the platinum layer is sputtered on the polymer graft.

20. The sensor of claim 18, further comprising an opaque analyte permeable membrane over at least a portion of the polymer graft and the platinum layer, wherein the opaque analyte permeable membrane is configured to (i) block light from passing beyond the polymer graft and the platinum layer and (ii) channel the analyte to the graft.

21. The sensor of claim 7, further comprising an opaque analyte permeable membrane over at least a portion of the polymer graft.

22. The sensor of claim 21, wherein the opaque analyte permeable membrane is configured to (i) block light from passing beyond the polymer graft and (ii) channel the analyte to the graft.

23. The sensor of claim 21, wherein the opaque analyte permeable membrane is hydrophilic.

24. The sensor of claim 21, wherein the opaque analyte permeable membrane is a hydrophobic material that is functionalized to be hydrophilic.

25. The sensor of claim 21, wherein the opaque analyte permeable membrane is a hydrophilic nylon membrane.

26. The sensor of claim 21, wherein the opaque analyte permeable membrane is porous polyethylene terephthalate (PET) membrane.

27. The sensor of claim 7, wherein the living animal is a human.

28. The sensor of claim 7, wherein the medium is interstitial fluid.

29. The sensor of claim 7, wherein the analyte is glucose.

30. The sensor of claim 7, wherein the analyte is oxygen.

31. The sensor of claim 7, wherein the indicator molecules are fluorescent indicator molecules.

* * * * *